(12) United States Patent
Hertz

(10) Patent No.: US 6,287,180 B1
(45) Date of Patent: Sep. 11, 2001

(54) HANDHELD APPARATUS FOR PROPELLING PARTICULATE MATTER AGAINST A SURFACE OF A PATIENT'S TOOTH, AND METHOD

(76) Inventor: Reuben Hertz, 2318 Sea Island Dr., Ft. Lauderdale, FL (US) 33301

( * ) Notice: Subject to any disclaimer, the term of this patent is extended or adjusted under 35 U.S.C. 154(b) by 0 days.

(21) Appl. No.: 09/196,498

(22) Filed: Nov. 21, 1998

Related U.S. Application Data (63) Continuation-in-part of application No. 08/517,339, filed as application No. PCT/US96/11696 on Jul. 15, 1996, now Pat. No. 5,839,946.
(60) Provisional application No. 60/073,824, filed on Feb. 5, 1998.

(51) Int. Cl.[7] ......................................... B24C 7/00
(52) U.S. Cl. ................................. 451/90; 451/99
(58) Field of Search ........................... 451/102, 90, 38, 451/99

(56) References Cited

U.S. PATENT DOCUMENTS

| | | | |
|---|---|---|---|
| 2,133,149 | 10/1938 | Poncelet | 51/8 |
| 2,441,441 | 5/1948 | Paasche | 451/90 |
| 2,577,465 | 12/1951 | Jones et al. | 51/8 |
| 2,641,087 | 6/1953 | Greiser | 51/12 |
| 2,696,669 | 12/1954 | Ikse | 32/28 |
| 2,725,684 | 12/1955 | Crowe | 451/90 |
| 2,744,361 | 5/1956 | Larson et al. | 51/11 |
| 3,164,153 | 1/1965 | Zorzi | 128/224 |
| 3,634,631 | 1/1972 | Greenstein | 451/90 |
| 4,369,607 | 1/1983 | Bruggeman et al. | 51/427 |
| 4,475,370 | 10/1984 | Stark et al. | 451/89 |
| 4,941,298 | 7/1990 | Fernwood | 451/99 |

Primary Examiner—Robert A. Rose
(74) Attorney, Agent, or Firm—Gerald E. Linden (57) ABSTRACT

A self-contained device is disclosed for directing a fluid stream containing particulate matter against a surface to abrade, etch, erase, cut, smooth, clean, polish and harden the surface. In tile preferred embodiments of the invention, the particulate matter is contained within the device and a carrier fluid, under pressure, introduced therein and mixes with the particles to produce a fluid stream that can be delivered to a target surface. The device can be powered and/or energized by a source of compressed gas which is coupled to the device through a fixture designed for that purpose. The invention also includes a method for delivery of a particle stream, under pressure, to a target surface, and, to tile selective modification of tile target surface depending upon the hardness of the particle, the velocity of impact thereof and the extent of the exposure of the target surface to tile particle stream.

20 Claims, 6 Drawing Sheets

HANDHELD APPARATUS FOR PROPELLING PARTICULATE MATTER AGAINST A SURFACE OF A PATIENT'S TOOTH, AND METHOD

This patent application is a continuation-in-part of U.S. patent application Ser. No. 08/517,379 filed Aug. 21, 1995 (status: issued Nov. 24, 1998 as U.S. Pat. No. 5,839,946), and claims benefit to U.S. Provisional Patent Application No. 60/073,824 filed Feb. 5, 1998; which is a continuation of PCT Patent Application No. PCT/US96/11696 filed Jul. 15, 1996 (status published as WO97/06924 Feb. 27, 1997).

BACKGROUND OF THE INVENTION

1. Field of the Invention

This invention relates to a device and to a method. More specifically, this invention is directed to a self-contained device for directing a fluid stream containing particulate matter against a surface to abrade, etch, erase, cut, penetrate, smooth, clean, polish and harden the surface. In one of the preferred embodiments of tile invention, the particulate matter is contained within the device, and a carrier fluid, under pressure, introduced therein to produce a fluid stream that can be delivered to a target surface. The device can be powered and/or energized by a source of compressed gas which is coupled to the device through a fixture designed for that purpose. The invention also includes a method for delivery of a particle stream, under pressure, to a target surface; and, to the selective modification of the target surface depending upon the hardness of tile particle, the velocity of impact and the extent of the exposure of the target surface to the particle stream.

2. Description of the Prior Art

The use of abrasives to modify tile surface of an object, (e.g., clean, polish, etch, etc.) is common practice in a variety of environments and professions. Typically such abrasive can take the form of a paste or free-flowing powder, and delivered to the surface of an object either manually, or through the use of a mechanical implement, or suspended in fluid (gas or liquid).

In the dental profession abrasives can be used to clean teeth and in the preparation of the dentition for bonding with various enamels and/or hardening agents. Typically the abrasive is delivered to the surface of the teeth by means of a carrier fluid stream (e.g., air or inert gas) containing a particulate abrasive. The object of such treatment is to remove foreign material, roughen or etch the surface to enhance bonding quality, or to dull an unsightly shine. As the gas and particulate matter impact the target material under pressure, the abrasive nature of the particles progressively causes layers of the target material to sheer one at a time. This process of controlled removal of material from the surface of the teeth is known as "etching".

Typically devices used in the delivery of the carrier fluid stream (e.g., air or inert gas) containing a particulate abrasive have resembled a sand blaster. More specifically, the generation of an abrasive fluid steam is accomplished by the placement of an abrasive in a reservoir and the drawing of the abrasive from the reservoir, under negative pressure, into an accelerated air or gas stream. The source of the accelerated air or gas stream) is typically a pressurized gas supplied from a compressor or tank.

In operation of the foregoing devices, the particle stream is directed through a channel of a nozzle (or delivery port) having a precise channel dimension and geometry. Typically this nozzle is constructed of metal or comparable durable material. As is appreciated, the precise delivery of the particle stream requires that the channel dimensions and geometry be maintained. Unfortunately, as the abrasive stream passes through the channel of the nozzle of the device, the inside diameter of the channel is worn (and the original tolerances altered), thereby causing a loss of precision, which ultimately requires the nozzle's replacement or replacement of the entire device. Additional maintenance is also required where, during the course of use, the device is exposed to debris or bacteria and thus must be cleaned prior to re-use. Because of the foregoing demands and constraints, such devices are typically expensive and thus are generally not readily discarded, even when in need of relatively extensive repair or refurbishing. Since such devices are not generally disposable, individuals must be skilled to maintain, clean, refill and reassemble them. This presents an opportunity for unit malfunction from contamination of the abrasive material, and by the reloading of the device with inappropriate and even dangerous particulate material.

Examples of these prior devices include that described in Fernwood, U.S. Pat. No. 4,941,298, issued on Jul. 17, 1990. Fernwood discloses a rear-reservoir micro sandblaster which includes a hollow tubular handle with a nozzle at one end for dispensing a mixture of a solid material and a gaseous medium, and a compressed air and solid particulate material-receiving member at the other end of the handle. The nozzle section of the apparatus contains a mixing chamber where a vacuum is created by the flowing pressurized gaseous medium, drawing solid material into the chamber from a rear reservoir Problems with Fernwood are that it is too costly to be disposable; it draws particulate matter from a container using a vacuum rather than by more efficient blow-through (turbulent or vortex) mixing of this gas as per the subject invention, and is thus very sensitive to variations in material and gas moisture levels, and requires an unclogging mechanisms, Fernwood also operates at relatively high pressures, 80–100 psi, requiring a special tap into the air lines and limiting the range of operational pressures. In addition, the Fernwood device suffers from one or more of the following perceived deficiencies:

- requires special training to set up and use,
- cannot deliver varying sizes of particles,
- is contaminated after every use, and
- is not cost-effective and cannot be completely sterilized between use.

The apparatus disclosed in the Microetcher™ brochure (available from [insert company and address]) is similar to the Fernwood device in that it suffers from most, if not all, of the same perceived deficiencies. Other products available from various manufacturers, are similarly limited, and/or otherwise attempt to differentiate themselves from their competition by offering "improvements" relative to ease of cleaning and/or sterilization, e.g., Handiblaster™, available from Mirage/Chameleon Dental Products, Inc., of [insert address]; and Microetcher II™, available from [insert supplier, address].

OBJECTS OF INVENTION

It is the object of this invention to remedy the above as well as related deficiencies in the prior art.

More specifically, it is the principle object of this invention to provide a device for delivery of a fluid particle stream which includes a combined particle reservoir and particle mixing chamber integral with such device.

It is another object of this invention to provide a device for precise delivery of a fluid particle stream that is both effective and yet inexpensive and thus readily disposable.

It is still another object of this invention to provide a device for precise delivery of a fluid particle stream that is pre-charged with particulate abrasive matter.

It is still yet another object of this invention to provide a device for precise delivery of a fluid particle stream which includes an adjustable dispensing conduit, or nozzle, for directing the flow of the fluid particle stream onto a delimited area of a target surface.

It is an additional object of this invention to provide a device for precise delivery of a fluid particle stream which includes means for introduction of the stream of fluid, under pressure, into a mass of abrasive particles within the device so as to create a turbulent mixture thereof that can be discharged via a dispensing conduit or nozzle onto a delimited area of a target.

It is an yet additional object of his invention to provide a method for precise delivery of a fluid particle stream to effect selective abrasion of a delimited area of a target.

SUMMARY OF THE INVENTION

The above and related objects are achieved by providing a device for the precision delivery of a particle stream of abrasive material to a delimited area of a target. In one of tile preferred embodiments of tile invention, the device comprises an essentially closed chamber having a fitting that is adapted for releasable connection to a source of pressurized fluid, means for directing the pressurized fluid into a mass of abrasive particles within the closed chamber so as to generate a mixture of fluid and abrasive particles within the closed chamber and a nozzle for delivery of the fluid and particle mixture to a delimited area of a target. Tile tern "fluid" as used herein is intended as inclusive of gases, liquids and any combination thereof. In the preferred embodiments of this invention, the source of gas is an air compressor, or pressurized canister containing air or an inert gas. The abrasive particles which are suitable for use in this device include aluminum oxide, sodium bicarbonate and other common polishing or grinding agents. The particle size of the abrasive should obviously be smaller than the any of the passages of the device through which they are to pass. The particle density is to a degree limited by the amount of pressure required to effect mixing thereof with the fluid in the chamber of the device and thereafter the transport/flow of the resultant mixture through the nozzle of the device.

The pressurized fluid is introduced into the chamber at or near the top of the device, and thereafter is directed through a fluid transport conduit to the base of tile device where it is forced through a free-flowing mass of particulate (abrasive) matter that has been predisposed within tile device at the time of its manufacture. Upon injection of the fluid into the chamber, turbulent mixing of fluid and abrasive particles occurs which mixture is and remains under substantial pressure (generally in excess of one (1) atmosphere). This is accomplished by control of the cross-sectional area of the fluid transport conduit relative to the cross-sectional area of the nozzle. The selection of a specific diameter for these two device components is a function of intended use, the particle size of the abrasive material to be delivery with such device and the desired force to be exerted upon tile target by the fluid particle stream as it is expelled from the end of the nozzle onto tile target surface. In the preferred embodiments of the invention, tile cross-sectional dimension of the fluid transport conduit is greater than the cross-sectional dimension of the nozzle. More specifically, the inside diameter of the conduit designed for dental applications is preferably at least about 50% greater than the cross-sectional area of the nozzle and can range from about 0.01" to about 0.20", with the most preferred diameter being about 0.045". the inside diameter of the nozzle can range from about 0.005" to about 0.100", with the preferred diameter being about 0.021".

In the preferred embodiment of the invention the nozzle comprises an elongated tube fixedly positioned in an orifice in the base of the chamber, and which extends both into and from the base of the chamber. Tile degree of extension of the distal end of the nozzle into the chamber is calculated to contribute and promote the formation of a turbulent mixture of fluid and particles in the chamber; and, the proximal end of tile nozzle, the precise delivery of the fluid stream containing the abrasive particles.

In one of the preferred embodiments of this invention the distal end of the nozzle is positioned near the top (lid) of the chamber, and above the open end of the fluid transport conduit. In addition, the relative height, or extension, of tile nozzle into the chamber is also a function of the volume of abrasive particles that is to be pre-loaded into tile chamber at tile time of manufacture. More specifically, it is preferable that the height of the nozzle extend at least above the level of the anticipated abrasive charge, and yet be sufficiently distant from the top (lid) of the chamber to allow for turbulent mixing and channeling of the mixture into the opening at the distal end of the nozzle.

The chamber design of the device is further unique in that it provides an effective and inexpensive configuration for the precise delivery of a fluid particle stream in a disposable package.

This invention also provides a method for propelling particulate matter against a surface of a target material using the above-described apparatus, including the steps of delivering a stream of fluid (e g. gas) into the fluid delivery conduit and from such conduit into the chamber of this device, so that tile flow of the gas stream continuously blows through the quantity of particulate matter, causing the particulate matter to mix with the gas stream, forming a gas and particle mixture, and discharging the mixture through the discharge conduit and the discharge port to strike tile surface of the target material.

BRIEF DESCRIPTION OF THE DRAWINGS

The drawings which are provided and described herein are intended to be illustrative of a number of the preferred embodiments of this invention. Where an element of an illustrated device is common to more than one drawing, it is assigned the same reference numeral for continuity of expression and ease of understanding.

DETAILED DESCRIPTION OF THE INVENTION INCLUDING PREFERRED EMBODIMENTS

The detailed embodiments of the invention disclosed herein are representative of a number of the preferred configurations of the device.

First Preferred Embodiment

Referring to FIGS. 1–4, a disposable particle-propelling apparatus 10 is disclosed for propelling particulate matter P against target material T. The apparatus 10 includes a cylindrical mixing chamber 16 having a chamber wall 20 and two end wall portions 22 (lid) and 24 (base), respectively. Apparatus 10 is powered by a compressed gas source, such as an air compressor or a compressed gas cylinder (not shown), which connects to and is in fluid communication with the gas receiving port 26 of end wall portion 22. The gas-delivery conduit 32 extends from the gas receiving port 26 into the mixing chamber 16. End wall 24 (base) has a mixture discharge port 34. A mixture discharge conduit 28 extends in fluid communication from mixture discharge port 34 into mixing chamber 16. A particle directing tube 36 is provided in fluid communication with discharge port 34 and extends opposite discharge conduit 28 outside from mixing chamber 16.

A quantity of particulate matter P is sealed inside chamber 16, the quantity being sufficient to only partially fill chamber 16, leaving space for gas and particulate matter P to mix. The complete sealing of the particulate matter P gives matter P a virtually unlimited shelf life and protection from contamination (e.g. humidity). Mixing chamber 16 provides a gastight seal to maintain particle sterility and to prevent gas leakage during operation. An inlet cap 42 and a tip cap 44 seal gas-receiving port 26 and mixture discharge port 34, respectively, and are removed when apparatus 10 is to be connected to the compressed gas source for use. Volume grid markings 46 are preferably provided on the wall side portion 20 of chamber 16 so that the quantity of particulate matter P used can be measured and visually observed when wall 20 is constructed of a transparent or translucent material. Chamber wall 20 may also be color-coded to identify the type of particulate matter P. The color code marking CC may indicate the particle size and the type of particulate matter P.

Tube 36 serves to both direct and accelerate the discharging gas and particular matter P mixture without the mixing chamber. As a result, the particulate matter P can be applied to a focused or delimited area of a target and at a uniform velocity. Since apparatus 10 is disposable, tube 36 can be fabricated inexpensively to sustain a limited use. Tube 36 is manually bendable (without crimping) thus permitting it to be quickly set to an angle without crimping, making the discharge omni-directional, and, thus, provide access to-hard-to-reach surfaces. Tube 36 preferably has a preset orifice diameter to accommodate a given size and type of particulate matter P, and is preferably made of metal, but may also be formed of suitable durable plastic or comparable material.

Chamber 16 is preferably an integrated chamber with balanced distribution of weight which is preferably slender enough to hold and manipulate as though it were a writing instrument. The direct, blow-through, turbulent mixing within chamber 16 makes apparatus 10 operational at all orientations relative to the target surface and to the direction of gravity. The slender construction makes chamber 16 able to access narrow spaces and operate in small confined areas. Chamber 16 can receive and function with varying gas pressures applied to gas-receiving port 26, selected to accelerate particles to various desired velocities for various given tasks, Turbulent mixing of particulate matters P directly in the path of the gas stream within chamber 16 enables apparatus 10 to deliver particulate matters P of a wide range of sizes, and to mix and deliver a wide range of particulate matter types. The direct, blow-through mixing in chamber 16, permits operation at very low pressures, thereby increasing the range of operational pressures which may be selected.

Apparatus 10 contains no moving parts and is preferably made of disposable plastic, so that particulate matter P and apparatus 10 can be sterilized at the factory, and apparatus 10 replaced rather than refilled and reused. Apparatus 10 is designed to withstand common sterilization techniques such as autoclave, chemical treatments and irradiation. Contemplated apparatus 10 construction materials may include but are not limited to plastic, stainless steel, Delrin™ and Teflon™. Apparatus 10 is light-weight, manufactured to be recyclable, and easy to use and replace without training or maintenance.

Figure 1:
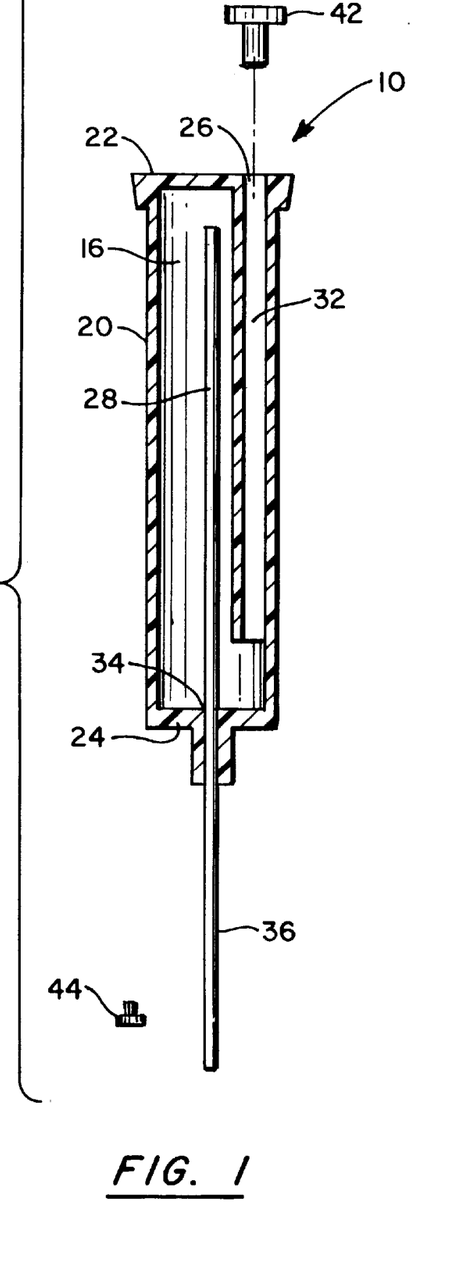
FIG. 1 is a cross-sectional side view of the preferred embodiment of the inventive particle-propelling apparatus. The particulate matter and gas source are omitted.
Figure 2:
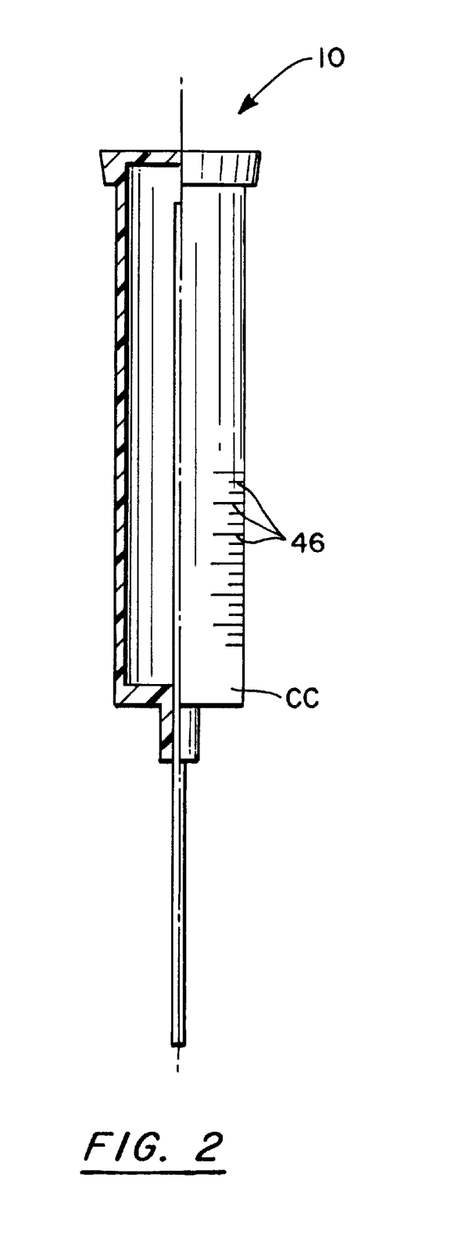
FIG. 2 is a partial cross-sectional side view of the apparatus of FIG. 1, revealing some of the outer chamber side wall having optional grid measuring markings and a circumferential color-code band.
Figure 2A:
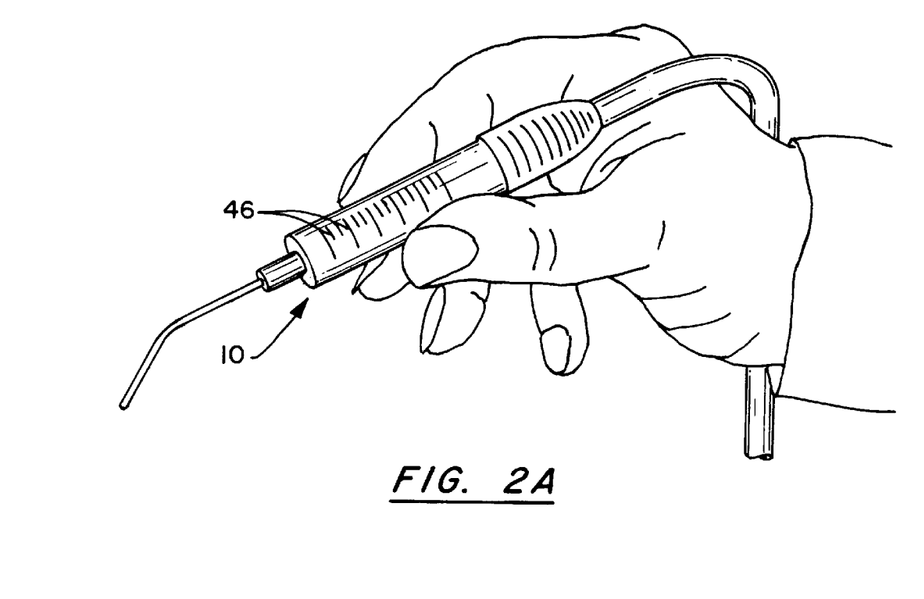
FIG. 2a is a perspective view of the apparatus of FIG. 2 in tile hands of a user ready for operation.
Figure 3:
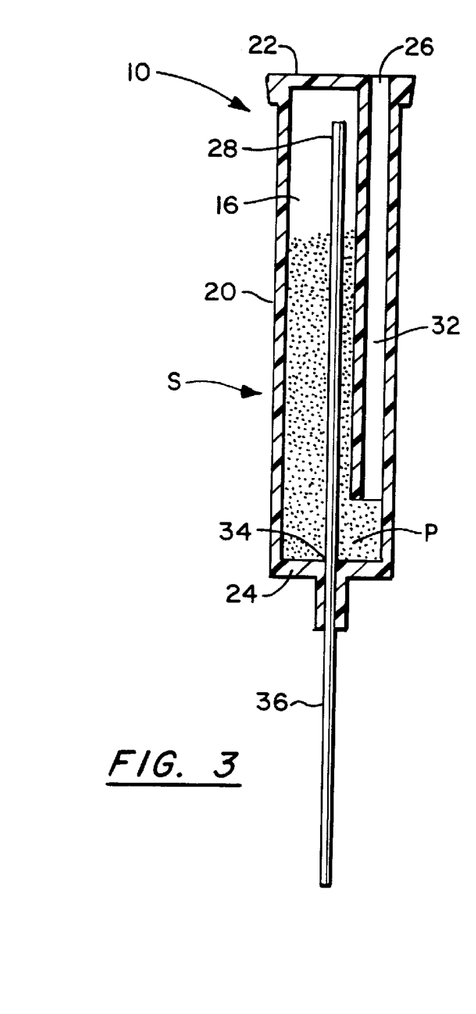
FIG. 3 is a view as in FIG. 1, showing the apparatus with the particulate matter added.
Figure 4:
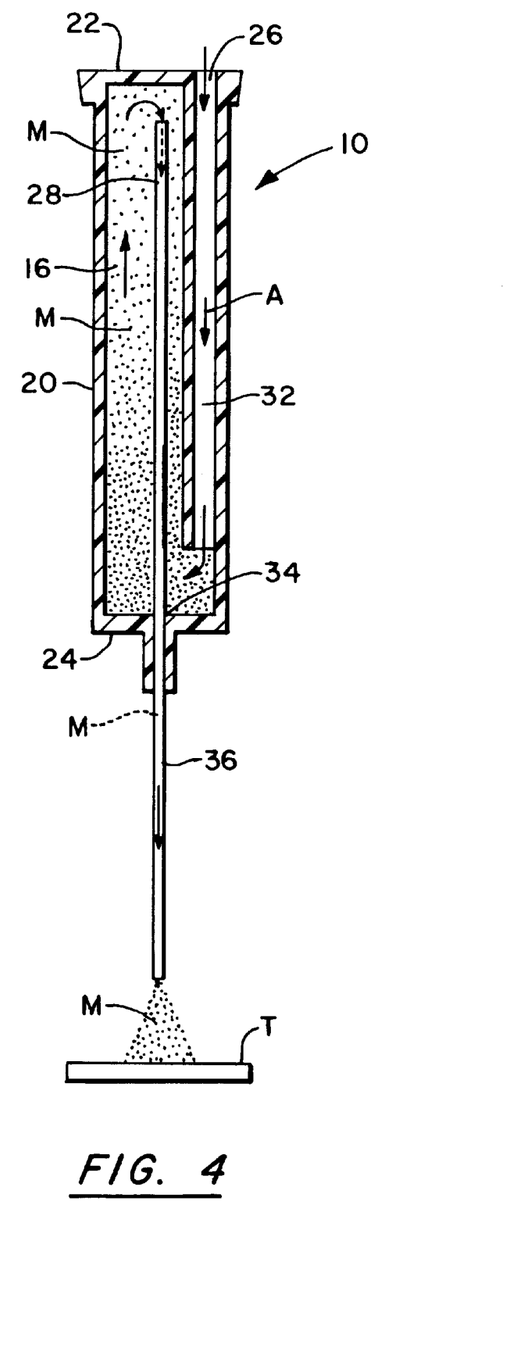
FIG. 4 is a view as in FIG. 3, with the apparatus in operation discharging the gas and particulate matter mixture toward a surface of a target material.
Figure 5:
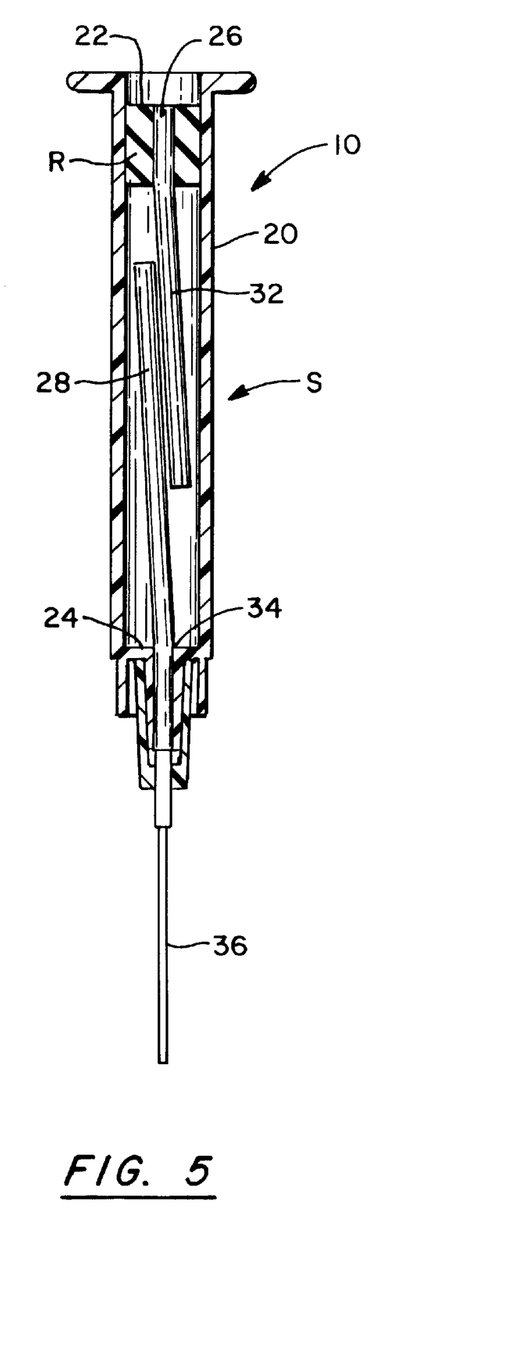
FIGS. 5 and 6 show alternative embodiments of the claimed apparatus, formed from a conventional industrial syringe.
Figure 5A:
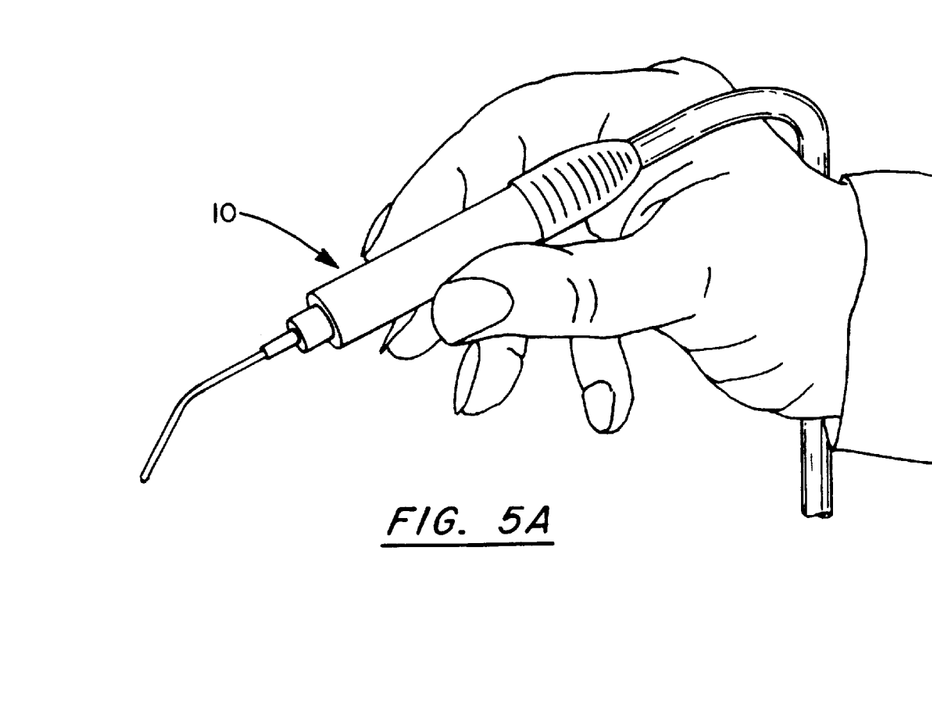
FIG. 5a is a perspective view of the apparatus of FIG. 5 in the hand of a user ready for operation.
Figure 6:
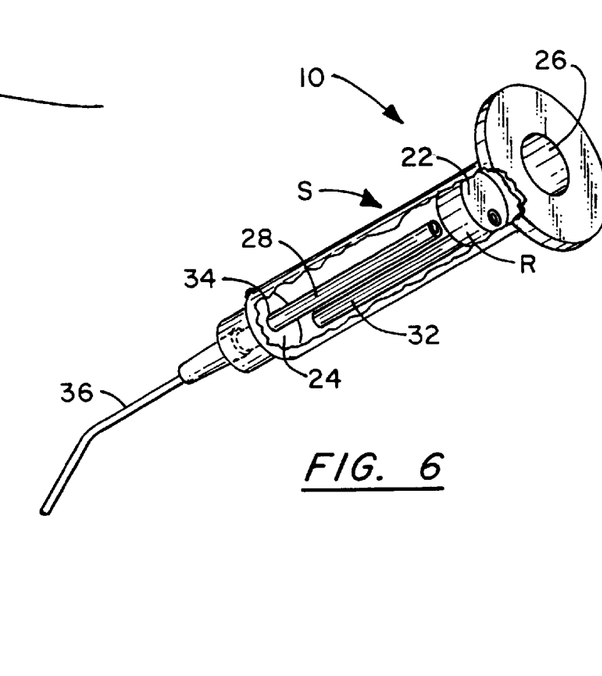

Apparatus 10 can be constructed from an adapted disposable syringe S of a type which is extremely common in the health care industry, see FIGS. 5 and 6. Needle 36 is attached to a standard syringe needle with a dulled tip, and formed of either metal or plastic. Gas-receiving port 26 is a hole bored into a standard rubber syringe stopper R separated from a standard syringe plunger. Mixture discharge port 34 is the existing discharge opening of the syringe S, while standard tubing can be used for gas delivery conduits 32 and 28.

Second Preferred Embodiment

Figure 7:
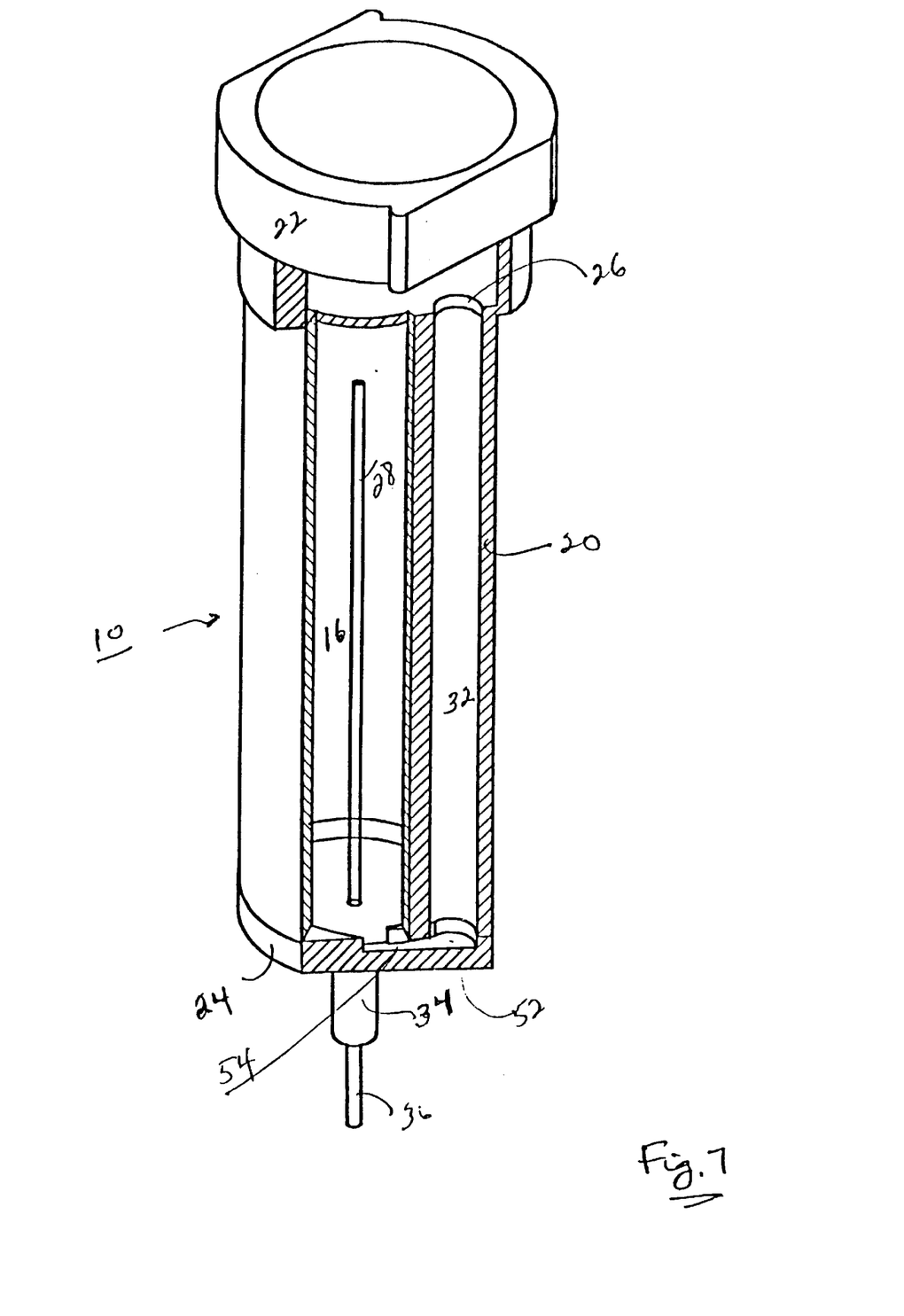
FIG. 7 is a perspective view, in partial section, of an alternative embodiment of the device of this invention in which a fluid delivery conduit is molded into the body of the device housing.

FIG. 7 depicts an alternative embodiment of the invention wherein the design choice of the various component parts thereof is based, in part, upon fabrication demands dictated by injection molding constraints and manufacturing economies. More specifically, tie fluid-deliver conduit (32) is fabricated as an integral component of the chamber wall (20). The fluid-deliver conduit (32) is further distinct from the First Preferred Embodiment described above in that such conduit now extends the full length of the chamber to the base (24) thereof The base (24) is also unique in that a chute (50) (as more fully illustrated in FIG. 8 described hereinafter) has been formed therein to provide for deflection of the fluid into the chamber so as to cause effective mixing of the fluid and the particle charge into a chute formed within the base of the chamber. This chute includes three distinctive functional features, namely an essentially round or bowl-like cavity (52) that roughly corresponds in overall dimension with the distal end of the fluid-delivery conduit (32). The second functional features comprises an intermediate section (54), or ascending ramp which is characterized by its progressive slope, that extends for the round or bowl-like cavity (52) to a riser (56) which directs the fluid into the chamber and thereby turbulence and/or a vortex within the chamber so as to effect mixing of (lie fluid with the free flowing particles that are contained therein.

Figure 8:
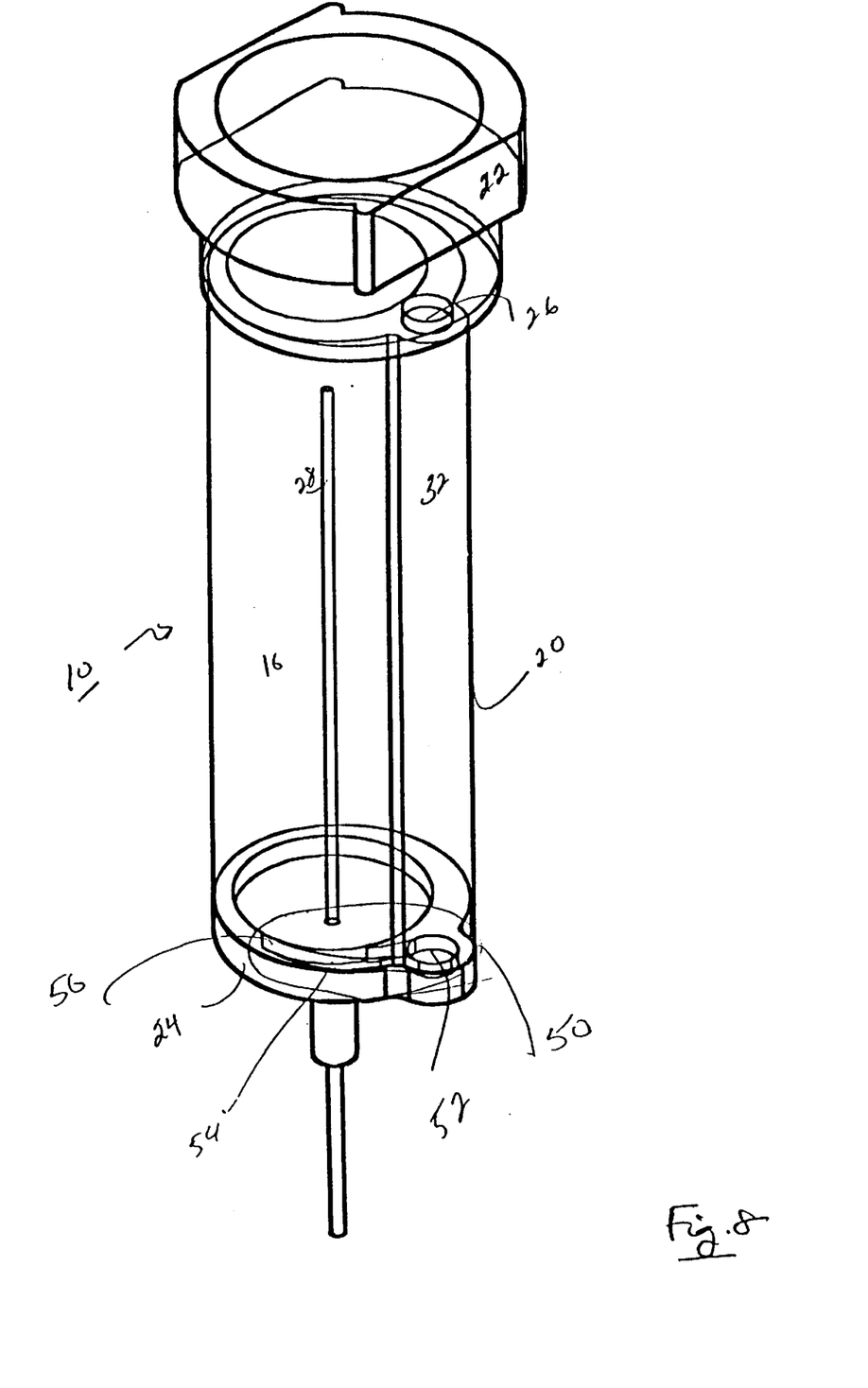
FIG. 8 is a perspective view of the device of FIG. 7 that has been molded from a transparent material.

FIG. 8 further illustrates additional detail of the construction of tile device of FIG. 7 wherein the interior of the base of the device is revealed. More specifically, FIG. 8 depicts a device of the type illustrated in FIG. 7 fabricated from a plastic material. In this view, tile detail of the base (24) is better revealed in that it further depicts the chute (50) and the ascending ramp (54) for channeling the fluid stream from the conduit into the chamber of the device. The chute can be modified as desired to optimize mixing and/or other operational objectives.

Method

In practicing the invention, the following method may be used. Reference is once again made to the illustrations of the preferred embodiments, specifically FIG. 4. A stream of gas A is delivered through gas-receiving port 26 and gas-delivery conduit 32 into chamber 16 from the gas air source (not shown). The gas stream A blows through the particulate matter P and causes the particulate matter P to mix with the gas stream in chamber 16. The air and particle mixture M enter and pass through discharge conduit 28, discharge port 34 and directing tube 36, and exist the apparatus 10 to strike the target material T, this method is performed without generating heat, vibration, appreciable noise levels, and with a device free of any moving parts. In contrast to the prior art devices discussed herein which draw the particulate matter from a reservoir, under vacuum, into a hand piece (and are thus limited as to the amount of pressure that can be exerted on the air/particle stream), the direct blow-through of fluid into the particle mass allows for modulation of the pressure of the resultant stream over a much broader range and thus more precise delivery thereof to a delimited area of a target.

In this manner there is provided a disposable apparatus powered by a compressed gas source for propelling particulate matter against a surface of a target material, more particularly against a surface of a dental patient's tooth, within the patient's mouth. The apparatus includes a mixing chamber having a chamber wall and a gas receiving port in the chamber wall in fluid communication with the compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber, wherein a stream of gas is delivered into the gas delivery conduit and into the mixing chamber from the gas source, the gas stream blows though the quantity of particulate matter and causes the particulate matter to mix with the gas stream in a mixing section of the chamber, forming a gas and particle mixture which enters and passes through the discharge conduit and the discharge port, and exits the apparatus to strike the surface of the patient's tooth.

The mixing chamber wall has a tubular side wall portion and two opposing end wall portions. The particulate matter does not completely fill said chamber. The chamber has a delivery conduit extending into the particulate matter. the chamber has a mixture discharge conduit extending into the mixing section of the chamber. A tubular particulate matter directing bendable tube is in fluid communication with the discharge port and extends outside and away from the chamber. The chamber may be formed of plastic, and may be color-coded to identify the particulate matter contained within the chamber.

Using this apparatus, particulate matter may be propelled against a surface of a target material by delivering a stream of gas into the gas delivery conduit and into the mixing chamber such that the gas stream blows through the particulate matter, thereby causing the particulate matter to mix with the gas stream, forming a gas/particle mixture, and discharging the gas/particulate mixture against a surface of the target.

While the various embodiments of the invention have been described and illustrated herein, such is not intended, nor should it be construed a delimiting the scope of the invention, which is set forth in the following claims.

What is claimed is:

1. In an apparatus for propelling a fluid mixture containing particulate matter, under pressure, against a surface of a target to effect controlled and selective modification of the surface of said target, wherein the improvement comprises:

a. an essentially cylindrical chamber having a side-wall, a lid at the top of the chamber and a base at the bottom of the chamber, wherein said lid is further characterized as having a fluid receiving port which is adapted for coupling to a source of fluid under pressure, and said base is further characterized as having a discharge port which is adapted for coupling to a nozzle, b. a fluid-delivery conduit having a proximal end and a distal end, wherein the proximal end of said conduit extends from the fluid receiving port of the lid into the chamber and said distal end of said conduit opens in to the chamber for delivery of a fluid into said chamber under pressure, c. a nozzle comprising a discharge conduit fixedly positioned in the discharge port of the base of the cylinder, said discharge conduit having an open proximal end and an open distal end, said proximal end of said discharge conduit extending from the base of the cylinder and into the cylindrical chamber above the level of the distal end of the fluid-delivery conduit, and d. a quantity of particulate matter within the chamber sufficient to cover the distal end of the fluid delivery conduit and yet insufficient to cover the proximal end of the discharge conduit;

whereby upon introduction of fluid, under pressure, through the fluid-delivery conduit into the chamber, the particulate matter within said chamber is caused to mix with said fluid, and the resultant fluid and particle mixture discharged through the distal end of the discharge conduit of said nozzle onto the surface of a target so as to effect modification of the surface of said target;

wherein each of said fluid-delivery conduit and said discharge conduit have an essentially circular cross-sectional area along their respective lengths, and the cross-sectional area of said fluid-delivery conduit is greater than the cross-sectional area of said discharge conduit.

2. The improvement of claim 1, wherein the particulate matter is selected from the group consisting of aluminum oxide, calcium carbonate and mixtures thereof.

3. In an apparatus for propelling a fluid mixture containing particulate matter, under pressure, against a surface of a target to effect controlled and selective modification of the surface of said target, wherein the improvement comprises:

a. an essentially cylindrical chamber having a side-wall, a lid at the top of the chamber and a base at the bottom of the chamber, wherein said lid is further characterized as having a fluid receiving port which is adapted for coupling to a source of fluid under pressure, and said base is further characterized as having a discharge port which is adapted for coupling to a nozzle, b. a fluid-delivery conduit having a proximal end and a distal end,
  wherein the proximal end of said conduit extends from the fluid receiving port of the lid into the chamber and said distal end of said conduit opens in to the changer for delivery of a fluid into said chamber under pressure,
c. a nozzle comprising a discharge conduit fixedly positioned in the discharge port of the base of the cylinder, said discharge conduit having an open proximal end and an open distal end, said proximal end of said discharge conduit extending from the base of the cylinder and into the cylindrical chamber above the level of the distal end of the fluid-delivery conduit, and
d. a quantity of particulate matter within the chamber sufficient to cover the distal end of the fluid delivery conduit and yet insufficient to cover the proximal end of the discharge conduit,
  whereby upon introduction of fluid, under pressure, through the fluid-delivery conduit into the chamber, the particulate matter within said chamber is caused to mix with said fluid, and the resultant fluid and particle mixture discharged through the distal end of the discharge conduit of said nozzle onto the surface of a target so as to effect modification of the surface of said target,
  wherein the cross-sectional area of said fluid-delivery conduit is at least 50% greater than the cross-sectional area of said discharge conduit.

4. The improvement of claim 1, wherein the distal end of said fluid-delivery conduit extends into the chamber to a level above the base of the chamber.

5. The improvement of claim 4, wherein the distal end of said fluid-delivery conduit extends into the chamber to below the level of particulate matter.

6. In an apparatus for propelling a fluid mixture containing particulate matter, under pressure, against a surface of a target to effect controlled and selective modification of the surface of said target, wherein the improvement comprises:
  a. an essentially cylindrical chamber having a side-wall, a lid at the top of the chamber and a base at the bottom of the chamber,
    wherein said lid is further characterized as having a fluid receiving port which is adapted for coupling to a source of fluid under pressure, and said base is further characterized as having a discharge port which is adapted for coupling to a nozzle,
  b. a fluid-delivery conduit having a proximal end and a distal end,
    wherein the proximal end of said conduit extends from the fluid receiving port of the lid into the chamber and said distal end of said conduit opens in to the changer for delivery of a fluid into said chamber under pressure,
  c. a nozzle comprising a discharge conduit fixedly positioned in the discharge port of the base of the cylinder, said discharge conduit having an open proximal end and an open distal end, said proximal end of said discharge conduit extending from the base of the cylinder and into the cylindrical chamber above the level of the distal end of the fluid-delivery conduit; and
  d. a quantity of particulate matter within the chamber sufficient to cover the distal end of the fluid delivery conduit and yet insufficient to cover the proximal end of the discharge conduit,
    whereby upon introduction of fluid, under pressure, through the fluid-delivery conduit into the chamber, the particulate matter within said chamber is caused to mix with said fluid, and the resultant fluid and particle mixture discharged through the distal end of the discharge conduit of said nozzle onto the surface of a target so as to effect modification of the surface of said target;
    wherein the distal end of said fluid-delivery conduit extends into a chute formed within the base of the chamber,
    said chute being characterized as including on one end thereof receiving means for receiving the distal end of the fluid-delivery conduit, and a ramp, which includes an intermediate section, having a progressive slope, that extends from said receiving means to a riser on the opposite end thereof,
    whereupon fluid from said conduit is caused to be directed by said chute to flow in and around said channel so as to effectively mix said fluid with particulate matter present therein.

7. The improvement of claim 1, wherein the fluid-delivery conduit has an essentially circular cross-sectional area and an inside diameter of from about 0.010" to about 0.200".

8. The improvement of claim 7, wherein the fluid-delivery conduit has an inside diameter of about 0.045".

9. The improvement of claim 1, wherein the discharge conduit has an essentially circular cross-sectional area and an inside diameter of from about 0.005" to about 0.100".

10. The improvement of claim 9, wherein the discharge conduit has an inside diameter of about 0.021".

11. The improvement of claim 1, wherein the fluid-delivery conduit is adapted for coupling to a source of gas under pressure.

12. The improvement of claim 1, wherein the fluid-delivery conduit is adapted for coupling to a source of liquid under pressure.

13. The improvement of claim 3, wherein the particulate matter has an average particle size suitable for use in the cleaning, polishing or etching of teeth.

14. The improvement of claim 13, wherein the particulate matter has an average particle size suitable for use in the cleaning, polishing or etching of teeth.

15. The improvement of claim 6, wherein the orientation of the chute directs fluid into the chamber so as to create a swirling or cyclone action therein.

16. The improvement of claim 3, wherein the distal end of said fluid-delivery conduit extends into the chamber to a level above the base of the chamber.

17. The improvement of claim 16, wherein the distal end of said fluid-delivery conduit extends into the chamber to below the level of particulate matter.

18. The improvement of claim 3, wherein the fluid-delivery conduit has an essentially circular cross-sectional area and an inside diameter of from about 0.010" to about 0.200".

19. The improvement of claim 3, wherein the discharge conduit has an essentially circular cross-sectional area and an inside diameter of from about 0.005" to about 0.100".

20. The improvement of claim 3, wherein the particulate matter is selected from the group consisting of aluminum oxide, calcium carbonate and mixtures thereof.

* * * * *